United States Patent [19]
June et al.

[11] Patent Number: 5,948,893
[45] Date of Patent: Sep. 7, 1999

[54] MURINE HYBRIDOMA AND ANTIBODY BINDING TO CD28 RECEPTOR SECRETED BY THE HYBRIDOMA AND METHOD OF USING THE ANTIBODY

[75] Inventors: Carl H. June; Nancy Craighead, both of Rockville, Md.

[73] Assignee: The United States of America as represented by the Secretary of the Navy, Washington, D.C.

[21] Appl. No.: 08/587,609

[22] Filed: Jan. 17, 1996

[51] Int. Cl.$^6$ .............................. C12N 5/00; C07K 16/00
[52] U.S. Cl. ................. 530/388.75; 530/388.22; 435/334; 435/346
[58] Field of Search ............. 435/240.23, 240.27, 435/975, 7.24, 70.4, 334, 346; 530/388.1, 391.3, 388.75, 391.1, 388.22

[56] References Cited

PUBLICATIONS

Kaye et al. (1995) J. Cell. Biochem. Supplement O(21A), 171.

Gross et al. (1992) J. Immunol, vol. 149: 380–388.

Baroja et al. (1989) Cell Immunol. vol. 120(1): 205–217.

Harding et al. (1992) Nature (Lond) vol. 356(6370): 607–609.

Johnstone et al. Immunochemistry in Practice. 2nd edition Blackwell Scientific Publications Oxford. 1987 pp. 232, 264–266.

*Primary Examiner*—Frank C. Eisenschenk
*Assistant Examiner*—Patrick J. Nolan
*Attorney, Agent, or Firm*—A. David Spevack

[57] ABSTRACT

The invention pertains to a murine hybridoma cell (ATCC HB 11944) that secretes a monoclonal antibody (PV-1) that binds to the CD 28 receptor. The antibody selectively stimulates the production of T-Cell populations to proliferate and expand in the absence of exogenous growth factors and accessory cells.

2 Claims, 10 Drawing Sheets

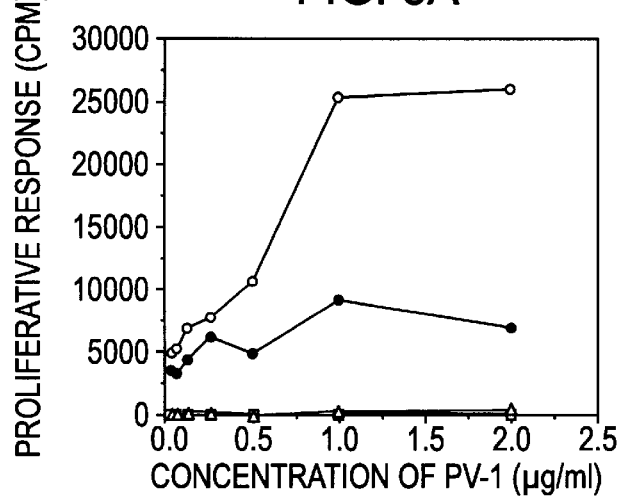
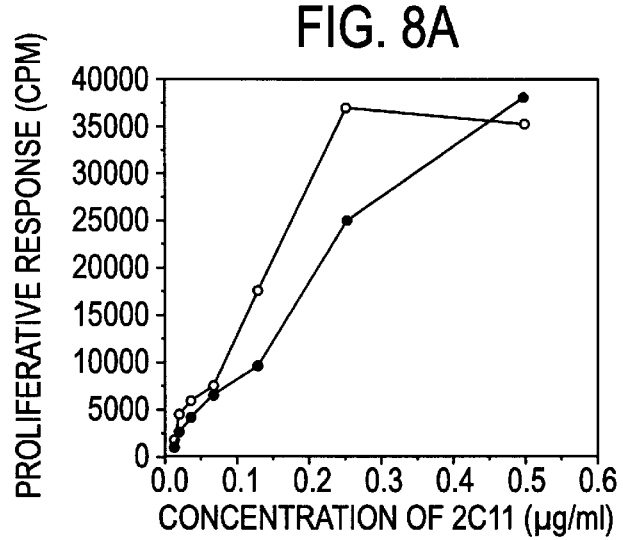
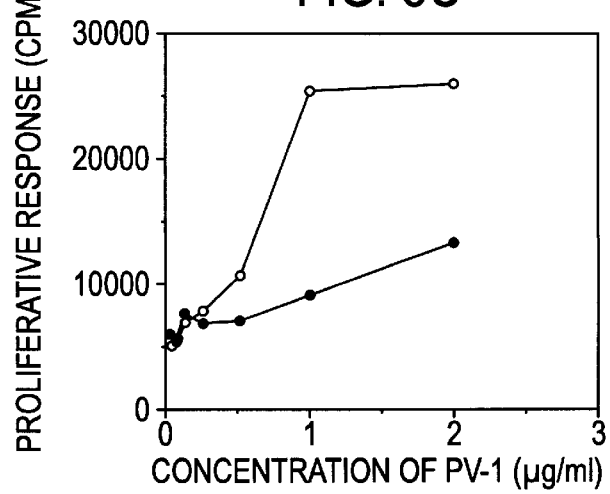

MURINE HYBRIDOMA AND ANTIBODY BINDING TO CD28 RECEPTOR SECRETED BY THE HYBRIDOMA AND METHOD OF USING THE ANTIBODY

BACKGROUND OF THE INVENTION

Field of the Invention

This invention relates to a murine hybridoma line that secretes a hamster monoclonal antibody that binds to the mouse CD28 receptor. The antibody has enhanced signal transduction properties compared to previously available reagents. The antibody permits ex vivo expansion of a population of T cells in the absence of exogenous growth factors, such as lymphokines, and accessory cells. The invention further pertains to methods of using the antibody and kits for providing the antibody.

Biological Deposit Information

The murine hybridoma cell line PV-1 is deposited in the American Type Culture Collection (ATCC), 10801 University Boulevard, Manassas, Va. 20110-2209 USA, under the terms and conditions of the Budapest treaty for a period of thirty (30) years. The registration number is HB 11944 supplemental deposit HB 12352. Under the terms of the deposit access to the culture will be available during pendency of the patent application to one determined by the Commissioner of Patents and Trademarks to those found to be entitled thereto under 37 CFR 1.14 and 35 U.S.C. 122, and all restrictions on the availability to the public of the culture will be irrevocably removed upon the granting of the Patent. The agreement with the ATCC provides in part, "The ATCC agrees that in consideration for a one-time service charge to preserve this culture and make it available for distribution . . . for a period of 30 years from the date of deposit, or until at least five years after the most recent request for a sample, which ever is longer.

Description of the Prior Art

The development of techniques for propagating T cell populations in vitro has been crucial to many of the recent advances in the understanding of T cell recognition of antigen and T cell activation. Techniques for expanding T cells in vitro have relied on the use of accessory cells and exogenous growth factors, such as IL-2. The requirement for MHC-matched antigen presenting cells as accessory cells presents a significant problem for long-term culture systems. An additional problem of current culture techniques is that they favor the growth of CD8 T cells at the expense of CD4 T cells. The binding of ligands to the CD28 receptor can bypass the need for addition of exogenous cytokines and enhance the activation of T cells, particularly CD4 T cells in vitro and in vivo. Antigen presenting cells are relatively short lived. Thus, in a long-term culture system antigen presenting cells must be continuously obtained from a source and replenished. An alternative culture method to clone and expand mouse CD4 T cells in vitro in the absence of exogenous growth factor and accessory cells would be of significant benefit.

SUMMARY OF THE INVENTION

This invention pertains to the production of a murine hybridoma line that secretes a hamster monoclonal antibody that binds to the mouse CD28 receptor. The antibody has enhanced signal transduction properties compared to previously available reagents. The antibody permits ex vivo expansion of a population of T cells in the absence of exogenous growth factors, such as lymphokines, and accessory cells. In addition, T cell proliferation can be induced without the need for antigen, thus providing an expanded T cell population which is polyclonal with respect to antigen reactivity. The antibody provides for sustained proliferation of a selected population of CD4$^+$ or CD8$^+$ T cells over an extended period of time to yield a multi-fold increase in the number of these cells relative to the original T cell population. The antibody causes selective signal transduction in subpopulations of T cells, and this may be related to the ability of the antibody to particularly enhance the growth of CD4 T cells.

To date, there is no information concerning the nature of CD28 signaling in mouse T cells. To investigate this, a monoclonal antibody PV-1, specific for mouse CD28 was produced. Immediate costimulatory events were studied by monitoring increases in T cell intracellular ionized calcium ($[Ca^{2+}]i$) and subsequent events were assessed by the appearance of activation gene products and cellular proliferation. It was found that splenic T cell costimulatory $[Ca^{2+}]i$ responses were significantly different from those resulting from TCR ligation. For example, whereas CD3 crosslinking readily induces $[Ca^{2+}]i$ elevation in resting T cells, $[Ca^{2+}]i$ elevation induced by CD28 crosslinking occured only with activated and not with resting T cells. Furthermore, despite the fact that TCR ligation induced nearly equivalent levels of $[Ca^{2+}]i$ elevation in both CD4$^+$ and CD8$^+$ T cells, CD28 ligation triggered $[Ca^{2+}]i$ elevation was restricted to CD4$^+$ T cells. The preferential responsiveness of CD4$^+$ T cells to CD28 signaling was also seen in the induction of CD69 and IL-2 receptor expression as well as in T cell proliferation. Thus the present results suggest distinct roles for CD28 in CD4$^+$ and CD8$^+$ T cell populations.

The PV-1 antibody described herein is useful to expand selected T cell populations for use in experiments that address autoimmunity, infectious diseases or cancer. The resulting T cell populations can be genetically transduced and used for immunotherapy or can be used for in vitro analysis of infectious agents. In addition, supernatants from cultures of T cells expanded in accordance with the PV-1 antibody are a rich source of cytokines and can be used to sustain T cells in vitro or ex vivo.

The present invention pertains to compositions comprising the PV-1 antibody as an agent that provides a preferred costimulatory signal to a T cell for T cell expansion. Furthermore, the invention provides for kits comprising the PV-1 antibody, including instructions for use, that are also within the scope of this invention.

BRIEF DESCRIPTION OF THE DRAWINGS

FIGS. 1A–F depict the characterization of PV-1 monoclonal antibody by immunoprecipitation and SDS-PAGE. (1A and 1B), CHO cells or CHO cells transfected with mouse (m) CD28 were surface labeled with $^{125}I$ by lactoperoxidase-catalyzed iodination. Membrane proteins were solubilized in lysis buffer containing 0.5% Triton X-100. Immunoprecipitation of $10^6$ cpm/sample was done with anti-CD28 mAb 57.31 (5 μg), PV-1 (5 μg), or protein A beads alone (Beads), followed by 10% SDS-PAGE under non-reducing (1B) or reducing (1A) conditions. (1C) EL4 cells were labeled, extracted in detergent buffer, and the detergent-soluble material subjected to immunoprecipitation. Eluted material was separated on 12% SDS-PAGE under reducing conditions, and detected by phosphorimagery (Molecular Dynamics, Sunnyvale, Calif.). The positions of molecular mass markers are indicated in kDa.

FIGS. 2A–B indicate that CD28 mAb PV-1 provides a costimulatory signal for proliferation and IL-2 production. Splenic T cells (1×10$^5$) were incubated on anti-CD3 mAb 2C11-coated (50 μg/ml, O--O) or control (PBS, ●--●) wells in the presence of various concentrations of soluble protein-A purified PV-1. 2A, Proliferation in the cultures after 72 hours as assessed by [$^3$H]thymidine incorporation. 2B, IL-2 secretion as measured after 48 hours using an IL-2 ELISA kit (Collaborative Biomedical Products, Bedford, Mass.). Points: mean of triplicate cultures.

FIGS. 3A–F demonstrate distinct patterns of $[Ca^{2+}]i$ mobilization after CD28 crosslinking by PV-1 and by TCR ligation. Splenic T cells were preincubated with PMA (10 ng/ml) overnight. T cells were loaded with indo-1 and then stained with biotin-anti-CD28 mAb(PV-1) (3A,B,C) or with biotin-anti-CD3 mAb(7D6) (3D,E,F). Streptavidin-Cy-chrome was added during the gap in analysis at the ~45–60 second point on the X axis to crosslink CD28 or CD3 mAbs. Data were collected by gating on cells that contain indo-1 and Cy-chrome fluorescence signals, explaining the increase in cells at the 1.25 min point. The $[Ca^{2+}]i$ response after CD28 ligation (3A) and CD3 ligation (3D) is shown by single-cell dot plots. Mean $[Ca^{2+}]i$ vs time is plotted in 3B and 3E. In panels 3C and 3F, the % cells responding with $[Ca^{2+}]i$>2 s.d. above baseline (solid lines), and the % Cy-chrome cells (----) after anti-CD28 (3C) or anti-CD3 (3F) stimulation is plotted.

FIGS. 4A–B show that CD28 ligation by PV-1 triggers the $[Ca^{2+}]i$ response in CD4$^+$ but not CD8$^+$ splenic T cells. Splenic T cells were preactivated with PMA (10 ng/ml) overnight. The cells were collected, loaded with indo-1 and stained with FITC-anti-CD4, PE-anti-CD8 and biotin-anti-CD28 mAb(PV-1) orbiotin-anti-CD3 mAb(7D6). 4A. 5-color flow cytometric analysis of the $[Ca^{2+}]i$ response of CD4$^+$ and CD8$^+$ T cell subsets after CD28 ligation and CD3 ligation. Indo-1 violet/blue fluorescence ratio vs time is displayed after gating for FITC, PE, and Cy-chrome fluorescence signals. CD4$^+$CD8$^-$CD28$^+$(upper left), CD4$^+$CD8$^-$CD3$^+$(upper right), CD4$^-$CD8$^+$CD28$^+$(lower left), CD4$^-$CD8$^+$CD3$^+$(lower right). 4B. Cells were counterstained with streptavidin-PE. Data represent PE-fluorescence intensity.

FIGS. 5A–D indicate that competence for CD28-mediated $[Ca^{2+}]i$ signaling is induced with suspension culture or with PMA treatment. Spleen T cells were tested for signal transduction immediately after isolation,or after overnight culture in complete medium, or after overnight treatment with various concentrations of PMA (indicated). T cells were loaded with indo-1 and then stained with FITC-anti-CD4, PE-anti-CD8, and biotin-anti-CD28 mAb (PV-1) or biotin-anti-CD3 mAb (7D6). Thus, by gating on cells that were FITC$^-$, PE$^+$, and Cy-chrome$^+$we observed the calcium response of CD4$^+$ cells induced by crosslinking either CD28 (5A), or CD3 (5C). Similarly, by gating on cells that were FITC$^+$, PE$^-$, and Cy-chrome$^+$ we observed the calcium response of CD8 cells induced by crosslinking either CD28 (5B) or CD3 (5D).

FIGS. 6A–D depict effects of antibody staining on the $[Ca^{2+}]i$ response of $CD4^+$ and $CD8^+$ cells to CD28 ligation. Splenic T cells were preactivated with PMA (10 ng/ml) overnight. T cells were loaded with indo-1 and were stained with either FITC-labeled anti-CD8 antibody (A6, B) or FITC-labeled anti-CD4 antibody (6C,D). After washing, T cells were incubated with biotinylated PV-1 mAb, washed, and flow cytometric calcium analysis done. CD28 ligation was carried out by the addition of streptavidin-Cy-chrome. Separate analysis showed that the baseline $[Ca^{2+}]i$ was 130 nM, and the peak mean $[Ca^{2+}]i$ was 180 nM (6A), 612 nM (6B), 483 nM (6C), and 180 nM (6D).

FIGS. 7A–B show that CD28 PV-1 mAb ligation induces IL-2R and CD69 in $CD4^+$ but not $CD8^+$ T cells. Nylon wool non-adherent T cells (NNT) ($3\times10^6$) were cocultured with irradiated nylon adherent cells ($3\times10^6$) in the presence of 4 μg of PV-1 or 2C11. Cells were harvested 24 h, 48 h, and 72 h after cultivation, and were stained with FITC-anti-CD8, PE-anti-CD4, and biotin-anti-UL-2R (7A) or biotin-anti-CD69 (7B). Cells were counterstained with streptavidin-Cy-chrome. Freshly isolated T cells: $CD4^+IL2R^+$:5.4%, $CD4^-IL2R^+$:0.9%, $CD4^+CD69^+$:5.1%, $CD4^-CD69^+$:6.2%.

FIG. 8A is a plot of a mixed lymphoyte reaction with PV-1 addition.

FIG. 8B is a plot of a mixed lymphoyte reaction with 2C11 addition.

FIG. 8C is a plot of a mixed lymphoyte reaction with PV-1 Fab fragment addition.

FIGS. 8A–C demonstrate that CD28-mediated ligation by PV-1 selectively augments the autologous MLR of $CD4^+$ T cells. $CD4^+$ T cells, $CD8^+$ T cells, and nylon adherent cells were obtained from BALB/c spleen cells (see Materials and Methods). Three$\times10^5$ $CD4^+$ or $CD8^+$ T cells were cultured with or without $3\times10^5$ irradiated nylon adherent cells. Seven days after cultivation, proliferation in the cultures was assessed by [$^3$H]thymidine incorporation. 8A. The effect of CD28 ligation on the autologous MLR. Varying concentrations of purified PV-1 were added to the cell cultures of: open circles, $CD4^+$ T cells+Nylon nonadherent cells; closed circles, $CD8^+$ T cells+Nylon nonadherent cells; open squares, $CD4^+$ T cell alone; open triangles, $CD8^+$ T cell alone. 8B. The effect of CD3 ligation on the autologous MLR. Varying concentrations of purified 2C11 were added to the cell cultures of: open circles, $CD4^+$ T cells+Nylon nonadherent cells; closed circles, $CD8^+$ T cells+Nylon nonadherent cells; triangles, $CD4^+$ T cells alone. 8C. PV-1 Fab fragment inhibits autoreactivity of $CD4^+$ T cells facilitated by CD28 ligation. Proliferative responses of $3\times10^5$ $CD4^+$ T cells+Nylon nonadherent cells to PV-1 in the presence (closed circles) or absence (open circles) of 10 μg/ml of PV-1 Fab fragment.

FIGS. 9A–B depict B7-dependent preferential proliferation of $CD4^+$ T cells after B cell coculture. Splenic $CD4^+$ T cells, $CD8^+$ T cells, and T cell-depleted B cell-enriched APC were prepared as in FIG. 8. 9A. One$\times10^5$ $CD4^+$ or $CD8^+$ T cells were cultured with $2\times10^5$ irradiated B cells in 96-well plates which were coated with various doses of anti-CD3 mAb 2C11. On day three, proliferation in the cultures was assessed by [$^3$H]thymidine incorporation. (open circles) $CD4^+$ T cells+B cells; (closed circles) $CD8^+$ T cells+B cells; (open triangles) $CD4^+$ T cells alone; (closed triangles) $CD8^+$ T cells alone. 9B. One$\times10^5$ $CD4^+$ T cells were cultured with $2\times10^5$ irradiated B cells in the presence of 5 μg/ml CTLA4-Ig (closed circles) or control fusion-Ig (open circles).

DETAILED DESCRIPTION OF THE INVENTION

Figure 1A:
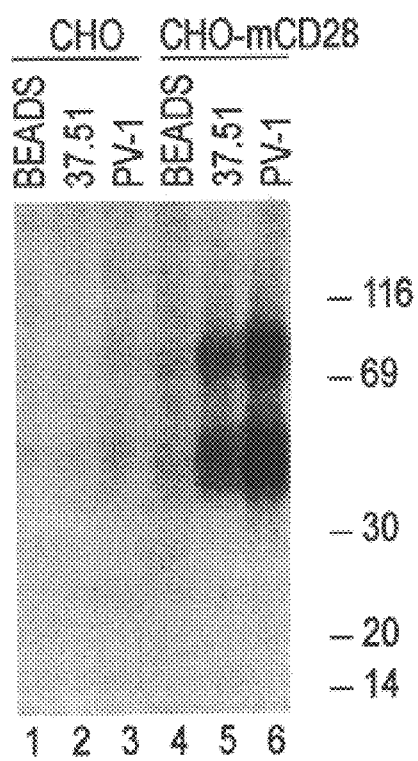
FIG. 1A is a computer generated image of the electrophoresis gel bands of immunoprecipitation of 10$^6$ cpm/sample done with anti-CD28 mAb 57.31 (5 µg), PV-1 (5 µg), or protein A beads alone (Beads), followed by 10% SDS-PAGE under reducing (A) conditions.

This invention describes the production of a murine hybridoma cell that secretes a hamster monoclonal antibody that binds to the CD28 receptor. Practical utility of the antibody is demonstrated in that it enables the selective stimulation of T cell populations to proliferate and expand to significant numbers in vitro in the absence of exogenous growth factors or accessory cells. This substantially decreases the expense of reagents and supplies for lymphocyte cultures. The term "T cell activation" is used herein to define a state in which a T cell response has been initiated or activated by a primary signal, such as through the TCR/CD3 complex, but not necessarily due to interaction with a protein antigen. A T cell is activated if it has received a primary signaling event which initiates an immune response by the T cell. T cell activation can be accomplished by stimulating the T cell TCR/CD3 complex. An anti-CD3 monoclonal antibody 2C11 (Leo et al. 1987, Proc. Natl. Acad. Sci. U.S.A. 84:1374–1378) can be used to activate a population of T cells via the TCR/CD3 complex. This antibody has been deposited with the American Type Culture Collection, Rockville, Md., catalog number CRL-1975. Additional antibodies can be prepared and identified by standard techniques.

A two-signal model of lymphocyte activation has been developed and refined by a number of investigators (Bretscher. 1992, Immunol. Today. 13:74–76). Although engagement of the T cell antigen specific receptor (TCR) by antigen/MHC products is essential for the initial stages of T cell activation, occupancy of the TCR alone does not induce proliferation of most primary T cells or T cell clones, but rather, induces antigen-specific unresponsiveness (Jenkins. 1992, Immunol. Today. 13:69–73) or T cell death (King and Ashwell. 1993, Curr. Opin. Immunol. 5:368–373). In addition to the first signal delivered as a result of TCR occupancy, a second signal, often termed a "costimulatory signal", is necessary for clonal expansion and functional differentiation of antigen-specific T cells. Recent studies indicate that this second signal can be delivered in vitro by the interaction between the B7 family of receptors on B cells (and other APCs) and the T cell CD28 receptor (Schwartz. 1992, Cell. 71:1065–1068; June et al. 1994, Immunol. Today. 15:321–331; June et al. 1990, Immunol. Today. 11:211–216).

The functional importance of CD28:B7 receptor interaction is further indicated by recent in vivo studies in mice and rats. Studies of CD28 receptor function using gene disruption to create a CD28-deficient mouse revealed pronounced and specific immune deficits (Shahinian et al. 1993, Science. 261:609–612). T cell development was normal in the CD28 (−/−) mouse, but peripheral T cells had impaired lymphokine secretion after stimulation with the lectin Concanavalin A, consistent with previous studies in normal T cells that had indicated a requirement for B7:CD28 interaction for mitogen activation. Studies using a soluble fusion protein CTLA4Ig that prevents CD28:B7 interaction indicate crucial roles of CD28:B7 interaction in T cell-dependent antibody production (Linsley et al. 1992, Science. 257:792–795), and in allo- and xenograft rejection (Lenschow et al. 1992, Science. 257:789–792; Lin et al. 1993, J. Exp. Med. 178:1801–1806; Turka et al. 1992, Proc. Natl. Acad. Sci. U.S.A. 89:11102–11105). In contrast, studies employing ectopic expression of B7 indicate that autoimmune illness can be induced through the breakdown of peripheral tolerance (Harlan et al. 1994, Proc. Natl. Acad. Sci. U.S.A. 91:3137–3141), and that syngeneic tumor rejection can be induced (Chen, Linsley, and Hellstrom. 1993, Immunol. Today. 14:483–486). Together, the above studies indicate that immunosuppression and antigen-specific tolerance can be induced by prevention of CD28 costimulation, while T cell-dependent immune responses can be evoked when CD28 receptor interaction is induced.

In human T cells, it has been shown that the binding of soluble antibody to CD28 in the context of TCR or CD2 ligation, or when combined with PMA treatment induces T cell proliferation and lymphokine production (June et al. 1990, Immunol. Today. 11:211–216). The enhanced lymphokine production by a CD28 signal has been shown to result in part, from the stabilization of lymphokine mRNA which is transcribed as a result of TCR-mediated signal transduction (Lindsten et al. 1989, Science. 244:339–343). On the other hand, although signal transduction by the TCR has been extensively investigated and well documented, the nature of intracellular signal transduction by costimulatory signals remains unclear. At least two distinct signals can be delivered through the CD28 receptor, depending on the degree of receptor oligomerization and the state of cellular activation (June et al. 1994, Immunol. Today. 15:321–331; June et al. 1990, Immunol. Today. 11:211–216). Of particular interest are the recent observations that signalling the CD28 pathway via the natural ligand, B7-1, can increase cellular tyrosine phosphorylation of several substrates (Vandenberghe et al. 1992, J. Exp. Med. 175:951–960; Lu et al. 1992, J. Immunol. 149:24–29), including phospholipase Cγ1 (Ledbetter and Linsley. 1992, Adv. Exp. Med. Biol. 323:23–27). In addition, CD28 can activate the lipid kinase, phosphatidylinositol 3-kinase (Truitt, Hicks, and Imboden. 1994, J. Exp. Med. 179:1071–1076; Ward et al. 1993, Eur. J. Imrunol. 23:2572–2577).

A primary activation signal can also be delivered to a T cell through use of a combination of a protein kinase C (PKC) activator such as a phorbol ester (e.g., phorbol myristate acetate) and a calcium ionophore (e.g., ionomycin which raises cytoplasmiccalcium concentrations). The use of these agents bypasses the TCR/CD3 complex but delivers a stimulatory signal to T cells. These agents are also known to exert a synergistic effect on T cells to promote T cell activation and can be used in the absence of antigen to deliver a primary activation signal to T cells.

Accordingly, to induce an activated population of T cells to proliferate (i.e., a population of T cells that has received a primary activation signal) in the absence of exogenous growth factors or accessory cells, an accessory molecule on the surface of the T cell, such as CD28, is stimulated with a ligand which binds the accessory molecule or with an agent which acts intracellularly to stimulate a signal in the T cell mediated by binding of the accessory molecule. In the embodiment, stimulation of the accessory molecule CD28 is accomplished by contacting an activated population of T cells with a monoclonal antibody which binds CD28. Activation of the T cells with, for example, an anti-CD3 antibody and stimulation of the CD28 accessory molecule results in selective proliferation of CD4$^+$ T cells.

Monoclonal Antibodies. The term "monoclonal antibody" as used herein, refers to a population of antibody molecules that contain only one species of an antigen binding site capable of immunoreacting with a particular epitope of an antigen. A monoclonal antibody composition thus typically displays a single binding affinity for a particular protein with which it immunoreacts. Preferably, the monoclonal antibody used is further characterized as immunoreacting with a specific protein.

Monoclonal antibody to an epitope of the CD28 antigen can be prepared by using a technique which provides for the production of antibody molecules by continuous cell lines in culture. These include but are not limited to the hybridoma technique originally described by Kohler and Milstein (Kohler and Milstein. 1975, Nature. 256:495–497). In one embodiment, the antibody preparation applied in the subject method is the monoclonal antibody PV-1 produced by a hybridoma cell line. Thus, the PV-1 monoclonal antibody composition of the present invention can be produced by the following method, which comprises the steps of:

(a) Immunizing an animal with a protein (e.g., CD28) or peptide thereof. The immunization is typically accomplished by administering the immunogen to an immunologically competent mammal in an immunologically effective amount, i.e., an amount sufficient to produce an immune response. Preferably, the mammal is a rodent such as a rat or mouse. A hamster is preferred as it is genetically diverse from the mouse, and more likely to yield antibodies to highly conserved proteins. The mammal is then maintained for a time period sufficient for the mammal to produce cells secreting antibody molecules that immunoreact with the immunogen. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay, e.g., a membrane associated form of the antigen (e.g., CD28). These screening methods are well known to those of skill in the art, e.g., enzyme-linked immunosorbent assay (ELISA) and/or flow cytometry.

(b) A suspension of antibody-producing cells removed from each immunized mammal secreting the desired antibody is then prepared. After a sufficient time, the mouse is sacrificed and somatic antibody-producing lymphocytes are obtained. Antibody-producing cells may be derived from the lymph nodes, spleens and peripheral blood of primed animals. Spleen cells are preferred, and can be mechanically separated into individual cells in a physiologically tolerable medium using methods well known in the art. The hamster spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques. These myeloma lines are available from the American Type Culture Collection (ATCC), Rockville, Md. The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. in Monoclonal Hybridoma Antibodies. Techniques and Applications Hurell (ed.) pp. 51–52 (CRC Press 1982)). Hybridomas produced according to these methods can be propagated in vitro or in vivo (in ascites fluid) using techniques known in the art.

Generally, the PV-1 cell line may be propagated in vitro for example in laboratory culture vessels, and the culture medium containing high concentrations of the specific CD28 monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al. (1959) Virol. 8:396) supplemented with 4.5 gm/l glucose, 20 mM glutamine, and 20% fetal calf serum. An exemplary inbred mouse strain is the Balb/c.

Animals and cell lines

BALB/c mice were purchased from The Jackson Laboratory (Bar Harbor, Me.) and Armenian hamsters were purchased from Cytogen (West Roxbury, Mass.). EL-4 and SP2/O were obtained from American Type Culture Collection (Rockville, Md.). Research was conducted adhering to the principles outlined in the Guide for the Care and Use of Laboratory Animals prepared by the Institute of Laboratory and Animal Research, National Research Council.

Reagents and Antibodies

The calcium indicator, indo-1 acetoxymethyl pentaester (indo-1) was obtained from Molecular Probes, Inc. (Junction City, Oreg.). PMA and ionomycin were obtained from LC Services Corp (Woburn, Mass.) and Sigma Chemical Co. (St. Louis, Mo.), respectively. All antibodies were pretitrated and used at saturating amounts for flow cytometric studies. Anti-CD8 (53-6.7) and anti-CD4 (GK1.5) monoclonal antibody (mAb) were obtained from American Type Culture Collection (Rockville, Md.). 145–2C11, hamster anti-mouse CD3, and 7D6, mouse anti-mouse CD3, were generously provided by J. Bluestone (University of Chicago, Chicago, Ill.) and Dr. O. Leo (University of Bruxelles, Belgium), respectively. CD28 antibody 37.51 (Gross, Callas, and Allison. 1992, J. Immunol. 149:380–388) was purchased from Pharmingen (San Diego Calif.). The soluble fusion proteins of CTLA4Ig and control fusion protein were produced as previously described (Gimmi et al. 1993, Proc. Natl. Acad. Sci. U.S.A. 90:6586–6590) and was kindly provided by Dr. Gary Gray (Repligen Corp, Cambridge, Mass.).

Generation of anti-mouse CD28 antibody, PV-1

Armenian hamsters were injected with $5 \times 10^7$ EL-4 cells twice i.p. and once i.v. Three days after the i.v. injection the hamsters were sacrificed and the splenocytes were fused with the SP2/O cell line using standard methods. After two cycles of limiting dilution at 1 cell per 3 wells in 96-well plates, culture supernatant from cloned cells was tested for binding to EL-4 by a modified cellular binding assay by ELISA. CD28 mAb PV-1 was identified by specific binding to mCD28-CHO cells, and was found to be of hamster IgG isotype.

Cell preparation and culture

Single cell suspensions were prepared from spleens. Spleen cells were applied to nylon wool columns and non-adherent cells (NNT) and adherent cells were collected as previously described (Okumura, Hayakawa, and Tada. 1982, J. Exp. Med. 156:443–453). Enrichment of $CD4^+$ $CD8^-$ or $CD4^-CD8^+$ T cells was performed using Dynabeads® M-450 (Dynal Inc., Oslo, Norway). Nylon wool non-adherent spleen cells were incubated with anti-CD4 (GK1.5) or with anti-CD8 (53-6.7) mAbs. After washing, cells were further incubated with anti-rat Ig coated Dynabeads® for 30 min at 4° C. with constant agitation, and the bound population was removed by application of a magnetic field. After enrichment, more than 90% of the T cells were $CD8^+$ or $CD4^+$. T cell-depleted B cell-enriched APC were prepared by treating spleen cells with anti-Thy-1.2+rabbit complement.

To assess DNA synthesis and IL-2 production of T cells by CD3 crosslinking, 96-well plates (Costar) were first coated with various concentrations of protein-A purified anti-CD3 mAb (2C11). Proliferation was assessed after 8–12 hr exposure to 1 $\mu$Ci [$^3$H]-thymidine. For measurement of IL-2 production, a mouse IL-2 ELISA kit (Collaborative Biomedical Products, Bedford, Mass.) was used according to the provided protocol.

Five Color Flow Cytometric Analysis of $[Ca^{2+}]_i$

NNT cells were incubated with 1 $\mu$M indo-1AM for 30 min at 37° C., washed, and resuspended in serum-free medium. Indo-1 loaded T cells were stained with PE-conjugated anti-CD4, FITC conjugated anti-CD8, and biotin-conjugated anti-CD3 (7D6) or anti-CD28 (PV-1) mAb for 20 min at room temperature. After two washes, equilibrated at 37° C., and analyzed using a Coulter Epics Elite® (Hialeah, Fla.). Streptavidin-conjugated Cy-chrome® (PharMingen, San Diego, Calif.) was added to crosslink molecules bound by biotin-labeled antibody. CD3 or CD28-positive cells were assessed by Cy-chrome fluorescence. The use of a fluorochrome-labeled crosslinking reagent permitted improved kinetic measurements, as the time between the washout of non-crosslinked cells in the fluidics system can be measured during each assay, by providing an internal "time stamp" for each experiment. This strategy should also permit the correlation of receptor occupancy with signal transduction thresholds. The 488 nm beam of an argon ion laser was used to collect narrow angle and right angle scatter information, and to excite fluorescence collected at 525 nm, 575 nm, and 670 nm from FITC, R-PE and Cy-Chrome, respectively. $PE^+FITC^-(CD4^+CD8^-)$ or $PE^-FITC^+$ $(CD4^-CD8^+)$ cells that were Cy-Chrome positive (i.e. $CD3^+$ or $CD28^+$ cells) were gated for analysis of calcium signals. The 325 nm beam of a helium-cadmium laser was used to excite indo-1, and the ratio of fluorescence emission at 395 nm and 525 nm was monitored. Data analysis was performed using the program MultiTime (Phoenix Flow Systems, San Diego, Calif.) as described previously (June and Rabinovitch. Current Protocols in Immunology, Chapter 5, pp 51–58, Greene Wiley Interscience, 1991).

Uses of the Invention

The cell line described in this invention can be used to produce an antibody specific for the mouse CD28 receptor. This antibody can be used to expand a population of $CD28^+$, CD4+, CD8+, mouse T cells for use in experiments regarding the treatment of infectious disease, cancer and immunotherapy. Anti-mouse CD28 monoclonal antibodies are difficult to obtain. The only other known antibody, 37.51 (Gross, Callas, and Allison. 1992, J. Immunol. 149:380–388) is less useful for signal transduction studies, cell staining, immunoprecipitation and cell expansion experiments. The data in FIG. 1 shows that the PV-1 antibody is superior for immunoprecipitation of mouse CD28.

Figure 2A:
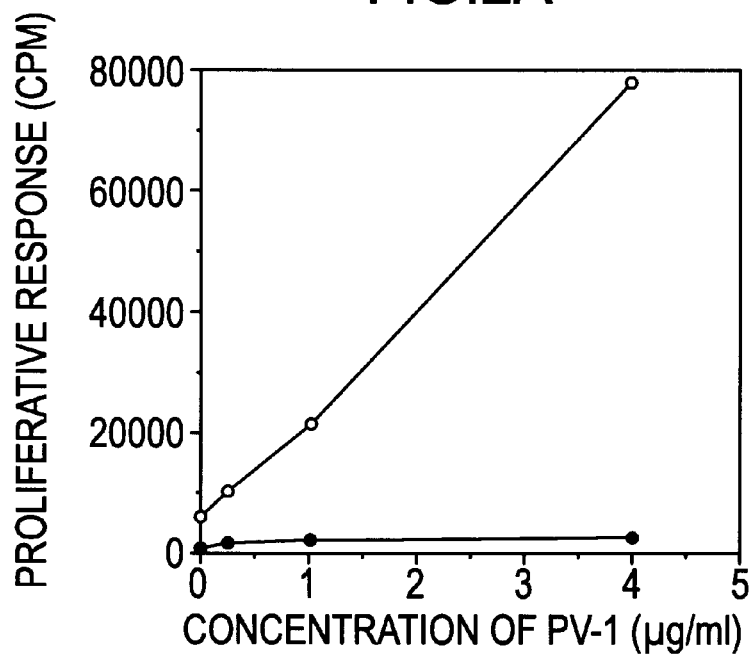
FIG. 2A is a plot of proliferation in the cultures after 72 hours as assessed by [$^3$H]thymidine incorporation. Points are the mean of the triplicate cultures.
Figure 2B:
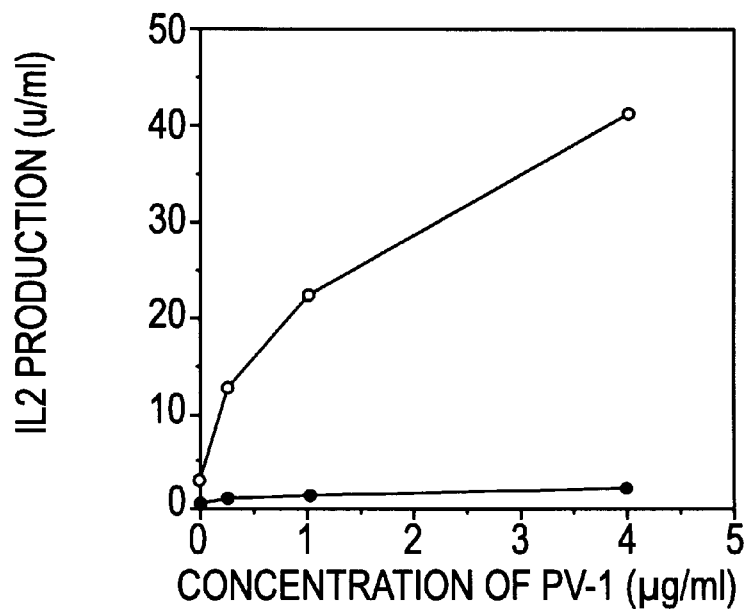
FIG. 2B is a plot of IL-2 secretion as measured after 48 hours using an IL-2 ELISA kit (Collaborative Biomedical Products, Bedford, Mass.). Points: mean of triplicate cultures.
Figure 3A:
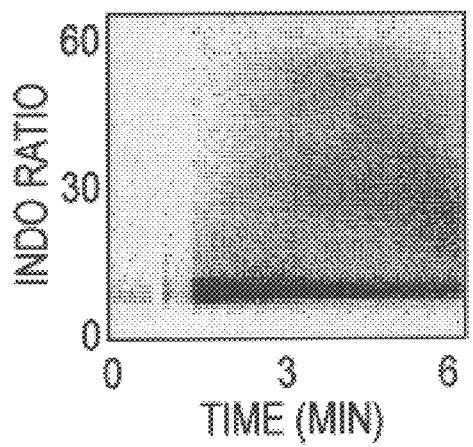
FIG. 3A is a computer generated image of the $[Ca^{2+}]_I$ response after CD28 ligation as shown by single-cell dot plots.
Figure 3D:
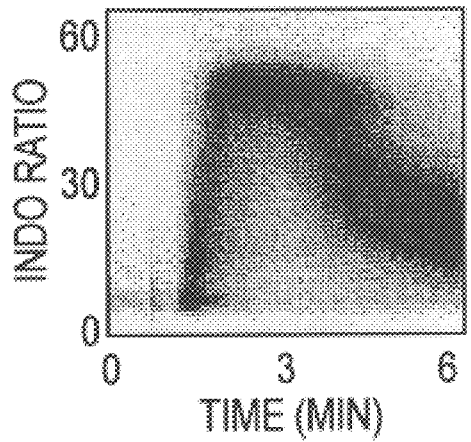
FIG. 3D is a computer generated image of the $[Ca^{2+}]_I$ response after CD3 ligation is shown by single-cell dot plots.
Figure 3B:
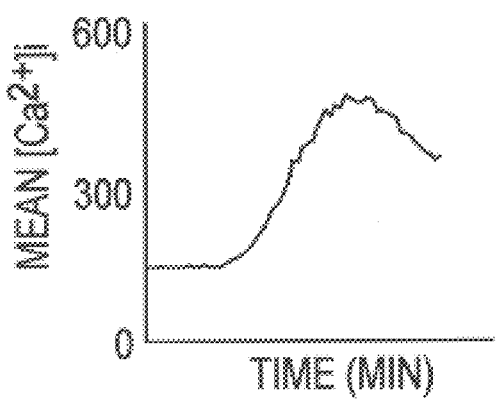
FIG. 3B is a plot of mean $[Ca^{2+}]_I$ vs time for the dot plot shown in FIG. 1A.
Figure 3E:
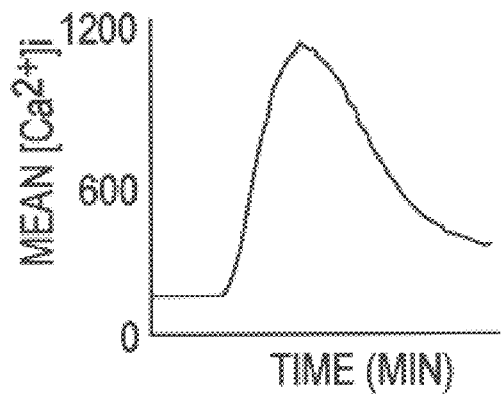
FIG. 3E is a plot of mean $[Ca^{2+}]_I$ vs time for the dot plot shown in FIG. 3A.
Figure 3C:
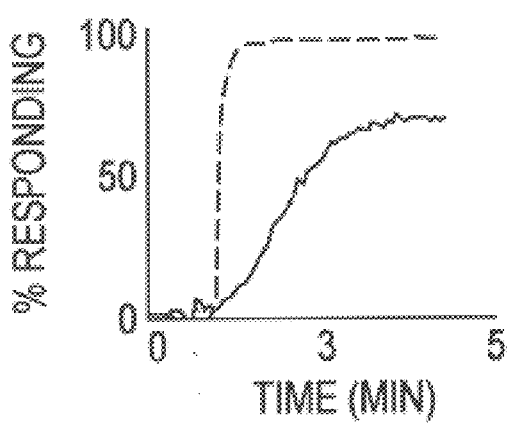
FIG. 3C is a plot of % cells responding with $[Ca^{2+}]_I$>2 s.d. above baseline (solid lines), and the % Cy-chrome+ cells (----) after addition of anti-CD28.
Figure 3F:
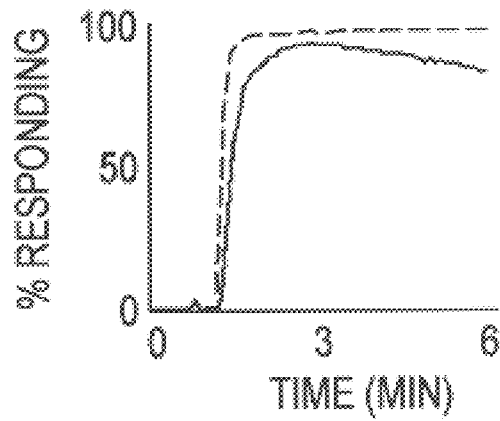
FIG. 3F is a plot of % cells responding with $[Ca^{2+1/}]$>2 s.d. above baseline (solid lines), and the % Cy-chrome+ cells (----) after anti-CD3 stimulation is plotted.

Another useful characteristic of this PV-1 hybridoma cell line is that it enables the production of large amounts of mouse cytokines from T cells. As shown in FIG. 2, large amounts of IL-2 are produced in tissue culture after addition of PV-1 to mouse T cells. In other experiments, large amounts of tumor necrosis factor and gamma interferon are also produced. In a related embodiment, the PV-1 antibody is useful to activate T cells for gene transduction or transfection experiments.

Another use of the hybridoma cell line is the production of PV-1 antibody for incorporation into a kit. Such kits could contain antibody labelled with fluorochromes such as phycoerythrin or fluorescein isothiocyanate for flow cytometric analysis or other forms of immunofluorescence. Another related use of the PV-1 antibody would be incorporation into kits with anti-CD3 antibodies. The preferred embodiment would be to co-immobilize the antibodies on beads. Beads could be polystrene or magnetic beads. These antibody-coated beads would be a valuable reagent for the growth of T cells in vitro and in vivo in mice.

This invention is further illustrated by the following examples which should not be construed as limiting. The contents of all references and published patent applications cited throughout this application are hereby incorporated by reference.

SPECIFIC EXAMPLES

Specific Example 1

Characterization of anti-murine CD28 antibody PV-1

Figure 1B:
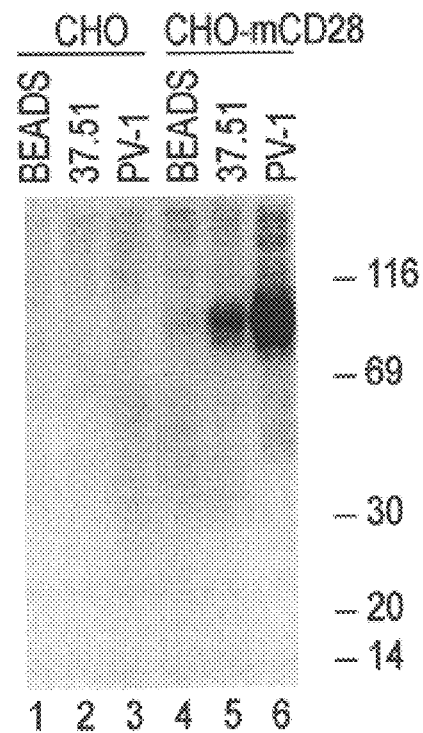
FIG. 1B is a computer generated image of the electrophoresis gel bands of immunoprecipitation of 10$^6$ cpm/sample done with anti-CD28 mAb 57.31 (5 µg), PV-1 (5 µg), or protein A beads alone (Beads), followed by 10% SDS-PAGE under non-reducing (B) conditions.
Figure 1C:
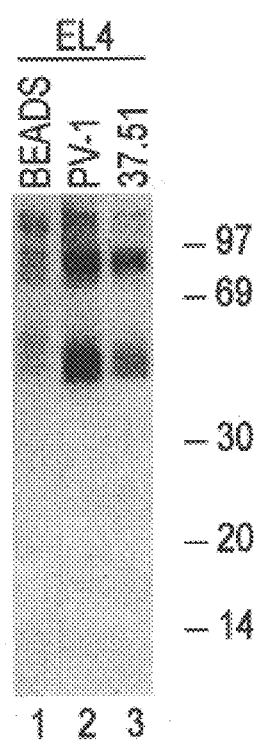
FIG. 1C is a computer generated image of EL4 cells labeled, extracted in detergent buffer, and the detergent-soluble material subjected to immunoprecipitation. Eluted material was separated on 12% SDS-PAGE under reducing conditions, and detected by phosphorimagery (Molecular Dynamics, Sunnyvale, Calif.). The positions of molecular mass markers are indicated in kDa.
Figure 1D:
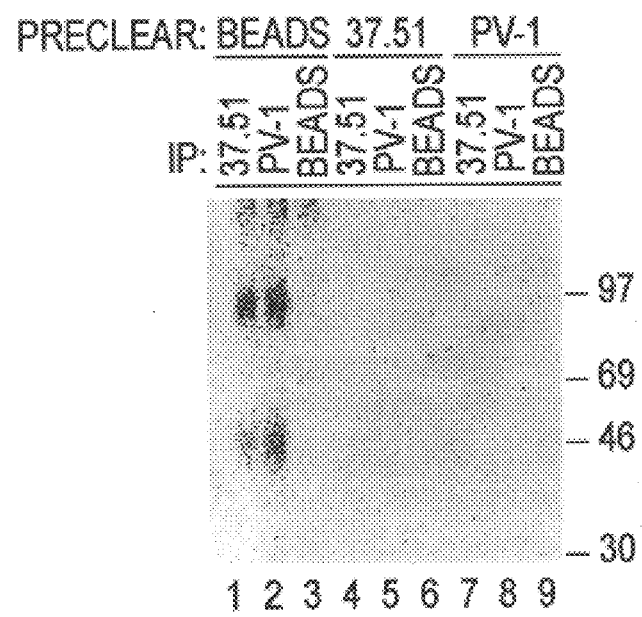
FIG. 1D is a computer generated image of splenic T cells activated with PMA, labeled, and precleared with 37.15 PV-1 or protein G-coated beads, then immunoprecipitated. Eluted material was separated on 12% SDS-PAGE under non-reducing conditions and detected by phosphorimagery (Molecular Dynamics, Sunnyvale, Calif.).
Figure 1E:
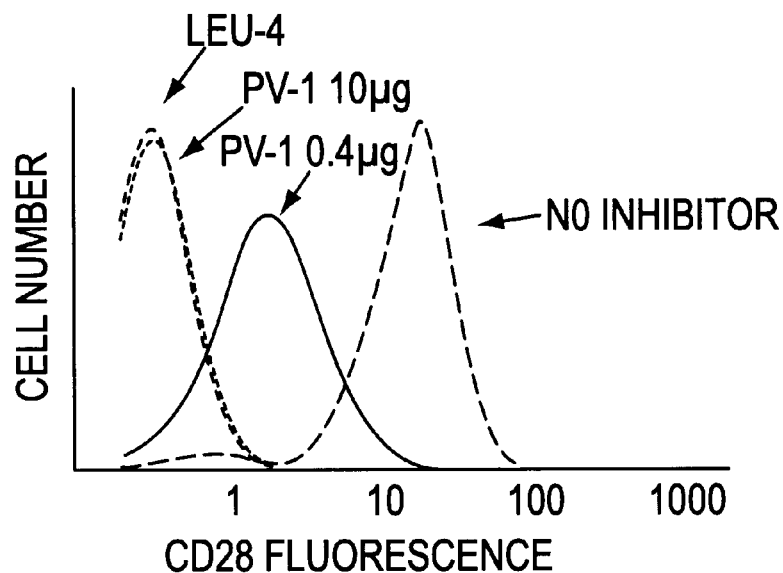
FIG. 1E is a flow cytometric plot of PMA activated splenic cells in the presence or absence of PV-1. Leu-4-PE acted as negative control.
Figure 1F:
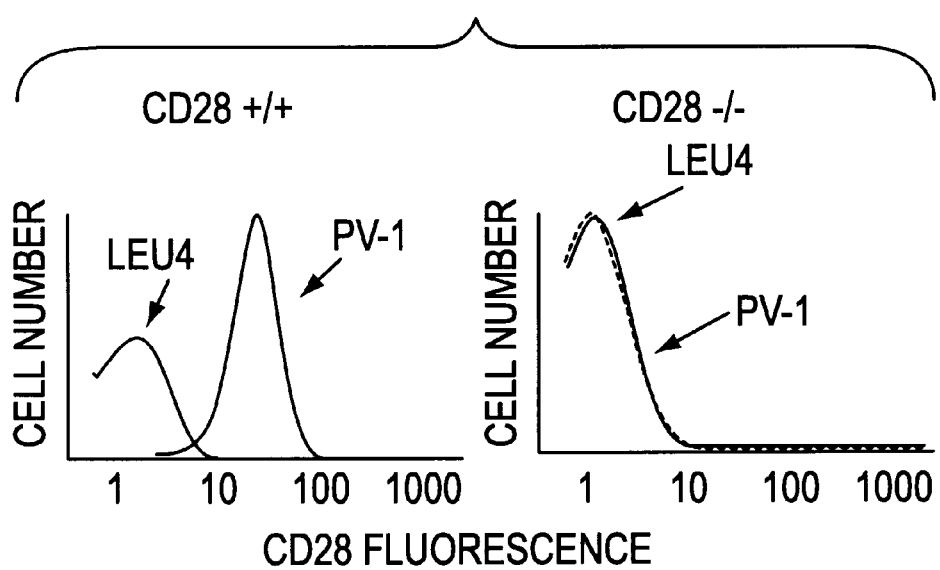
FIG. 1F is a flow cytometric plot of PMA-activated T cells from CD18 +/+ or CD28 –/+-Mice.

Hybridoma culture supernatants that bound EL-4 cells were tested for specific staining of the CHO cell line transfected with a mouse CD28 cDNA and with control CHO cells transfected with plasmid alone. A clone with specific binding to the mCD28-CHO cells, PV1.17.10 (PV-1), was selected and subjected to further characterization. Immunoprecipitation was carried out by the use of surface-radioiodinated cell lysates from EL-4, mCD28 and vector-transfected CHO cells. As shown in FIG. 1, PV-1 specifically precipitated broad bands that migrated at 40 kDa and 80 kDa in CHO cells transfected with mouse CD28 (FIG. 1A) and EL-4 (FIG. 1C) under reducing conditions, and a molecule of 80 kDa in CHO/mouse CD28 transfectants under non-reducing conditions (FIG. 1B). Material that co-migrated with PV-antibody specific for mouse CD28, 37.51 (Gross, Callas, and Allison. 1992, J. Immunol. 149:380–388). In crossblocking immunofluorecence studies, PV-1 mAb was found to prevent binding of 37.51 mnAb to mCD28-CHO cells (not shown). Finally, PV-1 did not bind to T cells from CD28 (−/−) mice (not shown). Together, these results confirm that the PV-1 mAb recognizes the product of the mouse CD28 gene.

Specific Example 2

Costimulatory effect of PV-1 on TCR-mediated activation of resting T cells

It has been shown that CD28 crosslinking results in the enhancement of T cell proliferation and IL-2 production when delivered in the context of TCR crosslinking or when accompanied by the pharmacologic agents PMA and ionomycin (Gross, Callas, and Allison. 1992, J. Immunol. 149:380–388; June et al. 1989, J. Immunol. 143:153–161). In order to explore the functional properties of PV-1, freshly isolated splenic T cells were cultured on plastic-immobilized anti-mouse CD3 mAb 2C11 in the presence of and in the absence of PV-1. As shown in FIG. 2, PV-1 stimulated T cell proliferation and IL-2 production in conjunction with sub-optimal anti-CD3 stimulation in a dose-dependent manner. Stimulation of purified T cells at rest with PV-1 alone was not mitogenic. These results are consistent with the previously reported studies on hCD28 (June et al. 1990, Immunol. Today. 11:211–216) and mCD28 (Gross, Callas, and Allison. 1992, J. Immunol. 149:380–388).

Specific Example 3

CD4+ T cells but not CD8+ T cells increase $[Ca^{2+}]i$ after CD28 crosslinking

Previous work demonstrated that CD28 ligation increased $[Ca^{2+}]i$ in activated human T cells (Ledbetter et al. 1990, Blood. 75:1531–1539) and in the Jurkat T cell line (Weiss, Manger, and Imboden. 1986, J. Immunol. 137:819–825). In addition, CHO cells that express B7 can induce tyrosine phosphorylation of phospholipase $C\gamma 1$ in activated T cells (Ledbetter and Linsley. 1992, Adv. Exp. Med. Biol. 323:23–27). In order to define the nature of mCD28 signal transduction, PMA-activated splenic T cells were loaded with indo-1 to permit analysis of $[Ca^{2+}]i$ levels, Under these conditions, neither the CD28 nor the CD3 reagent induced $[Ca^{2+}]i$ increases in the absence of additional crosslinking. CD28 or CD3 crosslinking was carried out by addition of Cy-chrome-conjugated streptavidin. Receptor crosslinking was assessed by the appearance Cy-chrome on the cell surface, and $[Ca^{2+}]i$ concentration was measured by the indo-1 fluorescence emission ratio. As shown in FIG. 3, there were significant differences between the CD3 and CD28 responses of splenic T cells. Essentially all cells responded to CD3 crosslinking, while only a subset of cells responded to CD28 crosslinking (FIG. 3, compare dot plots). Statistical analysis of the results shows that only 60 to 70% of cells responded to CD28 crosslinking whereas essentially all cells responded to CD3 crosslinking (FIG. 3, C vs F). A variety of time points and doses of CD28 stimulation were tested, and in all cases, a substantial population of non-responding CD28+ T cells was observed, unlike after anti-CD3 stimulation. In addition to crosslinking mCD28 with biotin-avidin, when second step anti-immunoglobulin reagents were used, a population of non-responding cells was still observed (data not shown).

In repeated experiments, the kinetic response of the CD28-stimulated cells was consistently delayed when compared to CD3 stimulation. This can be appreciated in the plots of mean $[Ca^{2+}]i$ vs. time (FIG. 3, B vs. E), as well as in the "gap" between the plots of the time course of Cy-chrome appearance and changes in mean $[Ca^{2+}]i$: 60 to 100 seconds are required for the CD28-induced calcium signal to reach the 50% of maximal $[Ca^{2+}]i$ after the saturation of biotin-CD28 sites, while there is virtual concordance of the two plots in the case of CD3 stimulation (FIG. 3 C vs. F).

Figure 4A:
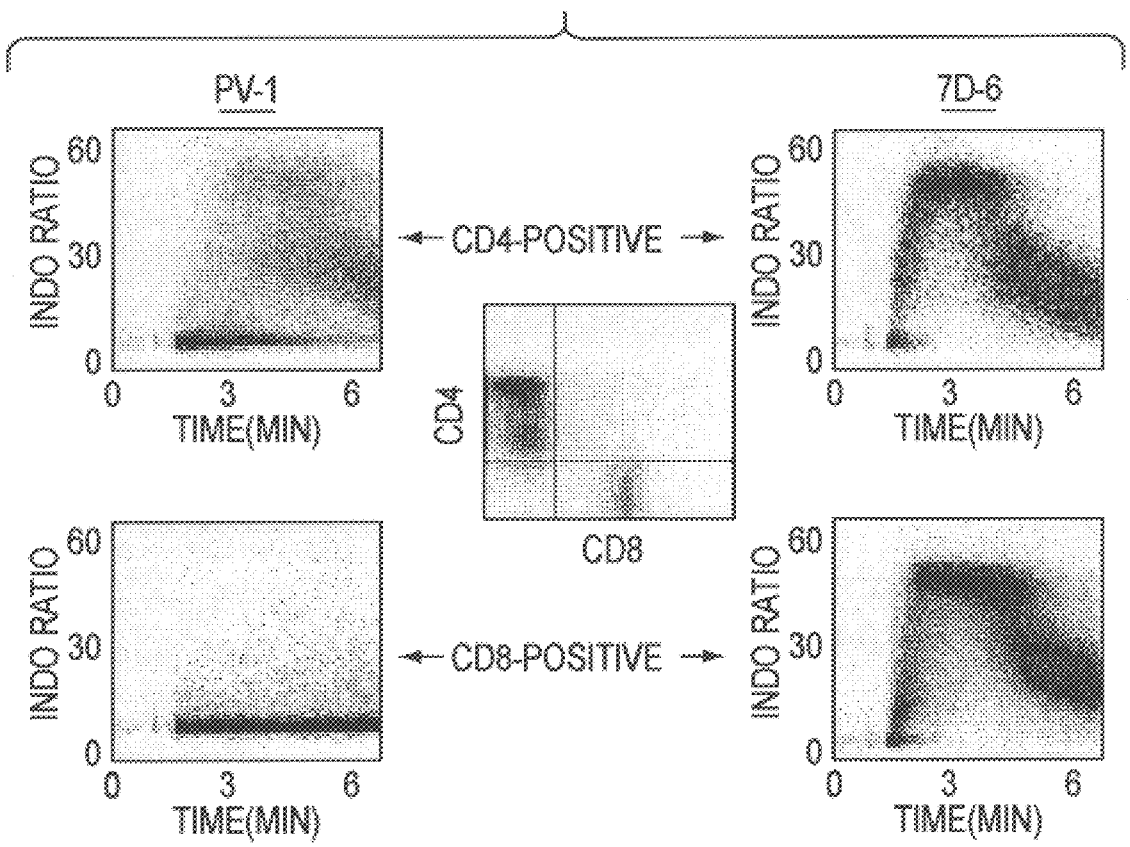
FIG. 4A is a computer generated image showing the calcium response of CD4 and CD8 splenic T cells after PV1 and 7D6 addition.

In order to characterize the T cell subset(s) responding to CD28 ligation with an increase in $[Ca^{2+}]i$, resting or PMA-activated T cells were first loaded with indo-1 and stained with FITC-conjugated anti-CD8 antibody, PE-conjugated anti-CD4 antibody, and biotinylated PV-1 or 7D6. CD28 or TCR ligation was carried out by crosslinking of these molecules with Cy-chrome-conjugated avidin. The $[Ca^{2+}]i$ response by $CD4^+$ or $CD8^+$ T cells was detected by gating on each subset, taking into account that all splenic T cells are $CD3^+CD28^+$ double-positive cells. TCR ligation again resulted in a large elevation of $[Ca^{2+}]i$ in >95% of both $CD4^+$ and $CD8^+$ T cells. In marked contrast, CD28-mediated $[Ca^{2+}]i$ elevation was restricted to the $CD4^+$ T cell subset (FIG. 4). At least 90% of $CD4^+$ T cells responded to CD28 crosslinking, indicating that the majority of activated $CD4^+$ T cells are susceptible to CD28-mediated $[Ca^{2+}]i$ signaling.

Figure 4B:
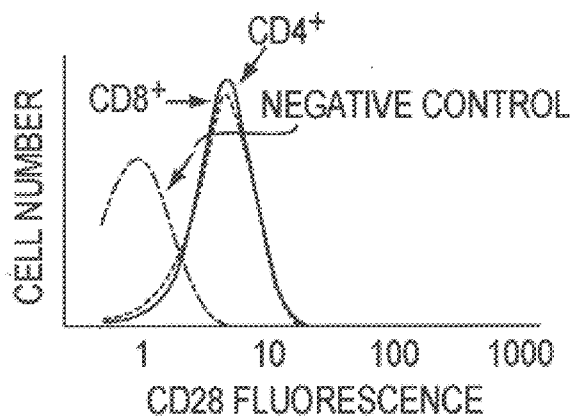
FIG. 4B is a plot of PV-1 staining and flow cytometry of CD4 and CD8 splenic T cells.
Figure 5A:
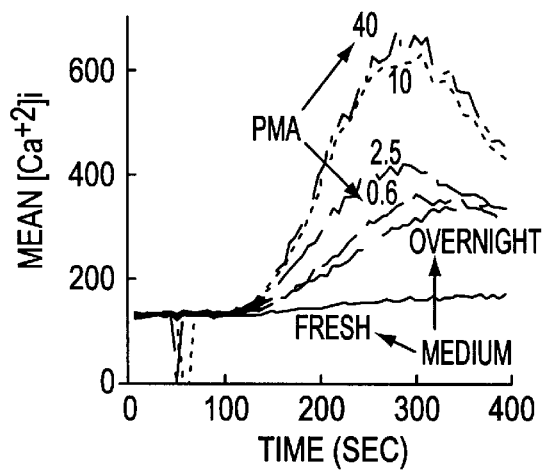
FIG. 5A is a plot of the mean calcium response in CD4 cells treated with various doses of PMA after CD28 ligation.
Figure 5B:
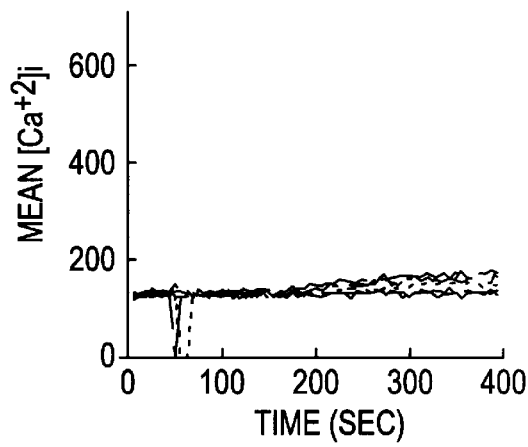
FIG. 5B is a plot of the mean calcium response in CD8 cells treated with PMA after CD28 ligation.
Figure 5C:
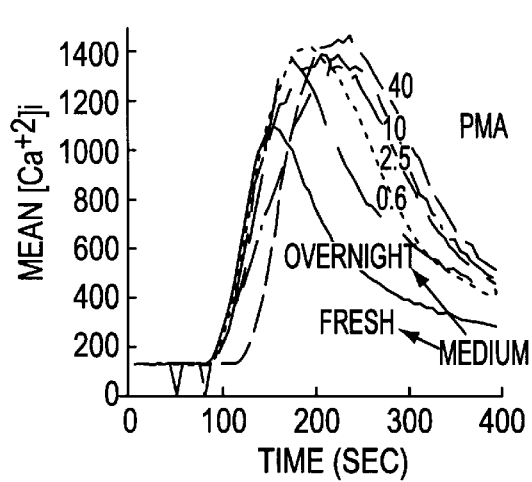
FIG. 5C is a plot of the mean calcium response in CD4 cells treated with PMA after CD3 ligation.
Figure 5D:
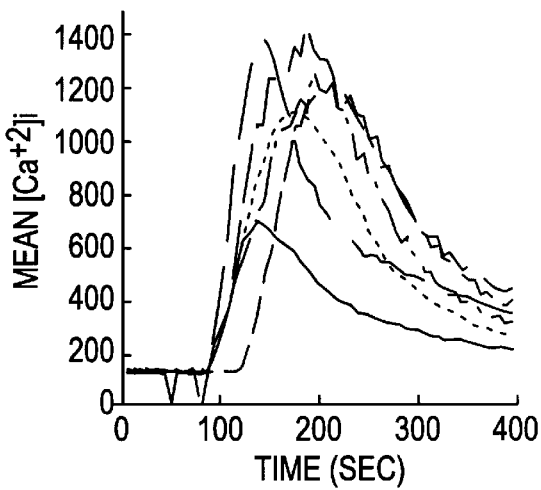
FIG. 5D is a plot of the mean calcium response in CD8 cells treated with PMA after CD3 ligation.
Figure 6A:
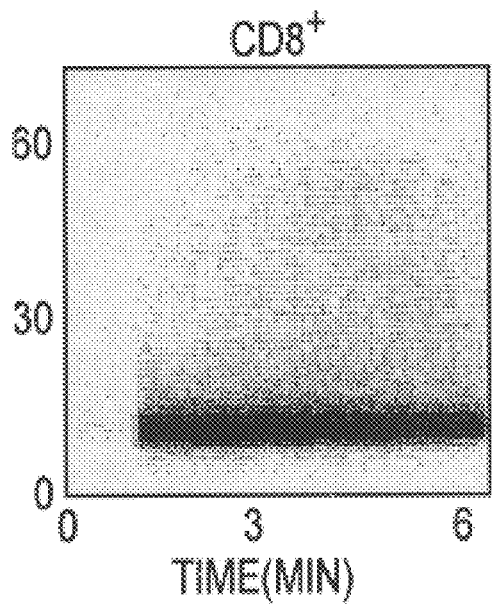
FIG. 6A is a computer generated image of CD8 cells stained with CD8-FITC and loaded with indo-1 and stimulated with PV-1.
Figure 6C:
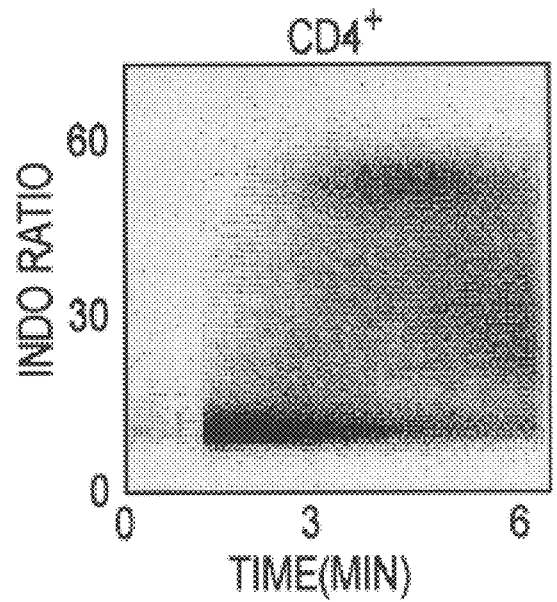
FIG. 6C is a computer generated image of CD8- cells stained with CD4-FITC and loaded with indo-1 and stimulated with PV-1.
Figure 6B:
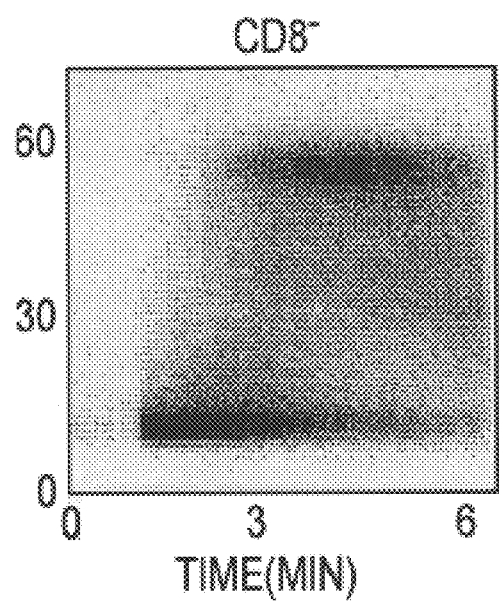
FIG. 6B is a computer generated image of CD4 cells stained with CD8-FITC and loaded with indo-1 and stimulated with PV-1.
Figure 6D:
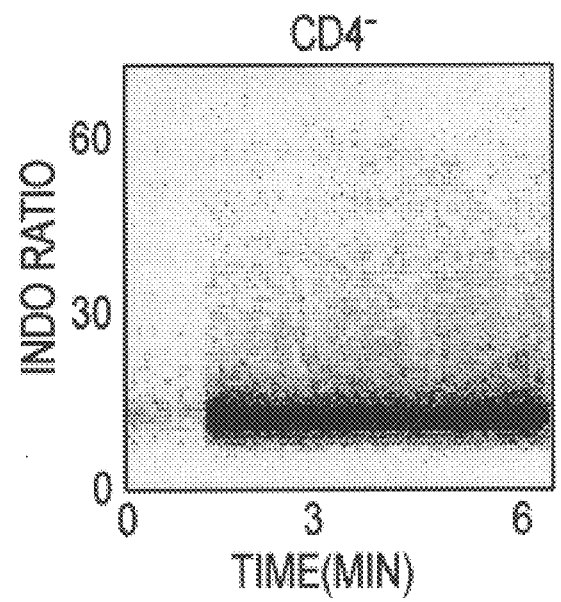
FIG. 6D is a computer generated image of CD4- cells stained with CD8-FITC and loaded with indo-1 and stimulated with PV-1.

One possible mechanism to account for the selective $[Ca^{2+}]i$ response of $CD4^+$ T cells could be the differential surface density of CD28 molecules on activated $CD4^+$ cells and $CD8^+$ cells. In order to address this possibility, splenic T cells were cultured overnight in the presence of 10 ng/ml of PMA and were tested the expression of of CD28 and CD3 by $CD4^+$ or $CD8^+$ T cell subsets. As shown in FIG. 4B, under this condition, there was no significant difference in CD28 expression on CD4 cells and on CD8 cells. This result excluded the possibility that differential CD28 signaling in $CD4^+$ and $CD8^+$ T cells is simply due to the different level of CD28 expression by these subsets.

As was noted above, freshly isolated mouse splenic T cells are not competent to respond to anti-CD28 stimulation. We considered the possibility that $CD4^+$ T cells might be more sensitive to activation by PMA than $CD8^+$ T cells. In order to test this possibility, T cells were activated with several concentrations of PMA, and the $[Ca^{2+}]i$ response of the $CD4^+$ and $CD8^+$ T cells was tested. As shown in FIG. 5, TCR ligation by CD3 crosslinking of freshly isolated T cells resulted in the elevation of $[Ca^2+]i$ in both $CD4^+$ and $CD8^+$ T cells, while these T cells were unresponsive to CD28 crosslinking. In contrast, PMA treatment induced CD28 receptor competence in the $CD4^+$ T cells, while $CD8^+$ T cells remained minimally responsive even after the highest doses of PMA pre-treatment. PMA treatment is not an absolute requirement for induction of CD28 responsiveness, as overnight suspension culture of T cells in complete medium without PMA could also induce CD28-mediated $[Ca^{2+}]i$ elevation, and this $[Ca^{2+}]i$ response was also restricted to the $CD4^+$ T cell population (FIG. 5). Together, the above results suggest that the CD28 receptor is not competent to transmit signals in freshly isolated T cells, and that the acquisition of competence is differentially regulated in T cell subsets. Furthermore, the preferential responsiveness of CD28-mediated $[Ca^{2+}]i$ signals in $CD4^+$ T cells can not be attributed to differential susceptibility of $CD4^+$ and $CD8^+$ T cells to PMA.

In the above experiments, T cell subsets were identified by positive selection. Given that previous studies have shown that TCR signal transduction can be influenced by CD4 and CD8 co-receptor crosslinking, it was possible that the binding of these antibodies to their targets may influence signal transduction through CD28. In order to test this possibility, PMA-activated splenic T cells were stained with either FITC-labeled anti-CD8 mAb or with FITC-labeled anti-CD4 mAb, and the $[Ca^{2+}]i$ response of the FITC-negative cells was assessed (FIG. 6). $CD8^-$ T cells ($CD4^+$) but not $CD4^-$ T cells ($CD8^+$) showed pronounced $[Ca^{2+}]i$ elevation after CD28 stimulation. This result is consistent with the previous experiments where T cell subsets were identified by positive selection, and indicates that the particular responsiveness of CD4 cells to CD28 is an intrinsic property of this T cell subset.

Specific Example 4

Figure 7A:
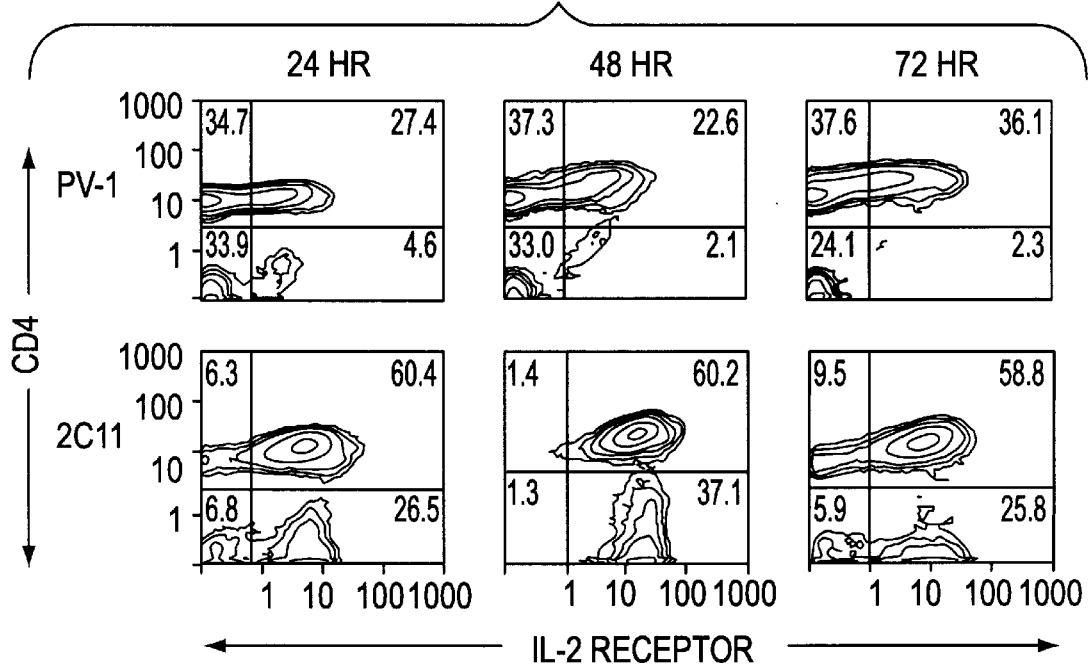
FIG. 7A is a flow cytometric plot of IL-2 receptor expression on CD4 cells after 24 to 72 hours of culture.
Figure 7B:
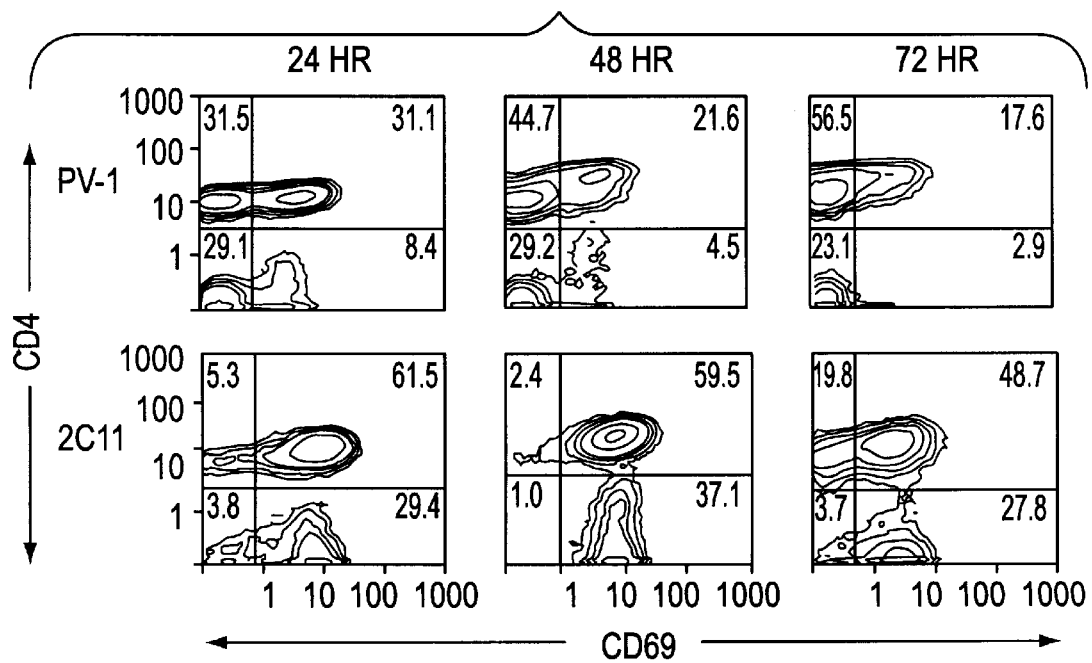
FIG. 7B is a flow cytometric plot of CD69 expression on CD4 cells after 24 to 72 hours of culture.

Distinct effects of CD28 stimulation on intermediate activation events in $CD4^+$ and $CD8^+$ T cell subsets In preliminary experiments, we found that an autologous MLR could be augmented by PV-1 mAb. To determine whether the skewing of CD28-induced signal transduction to the $CD4^+$ T cell subset was reflected in downstream activation events, splenic T cells were cultured with PV-1 or 2C11 in the presence of syngeneic irradiated APC, and the expression of IL-2 receptor α chain (CD25) and CD69 by $CD4^+$ or $CD8^+$ T cells was analyzed (FIG. 7). Cultured cells were harvested 24 h, 48 h, and 72 h after cultivation. Live cells were separated by density gradient centrifugation, and were stained with CD4- and CD8-specific antibodies, and then further stained with CD25-specific (FIG. 7A) or with CD69-specific (FIG. 7B) antibody. In T cell populations stimulated with 2C11, almost all T cells including both $CD4^+$ and $CD8^+$ T cells expressed IL-2R, and expression of IL-2R by both populations reached a peak at 48 h. In contrast, it was found that in T cell populations cultured with PV-1 alone, about half of the $CD4^+$ T cells expressed IL-2R, and that CD28-induced IL-2R expression was confined to the CD4 T cell subset. Similarly, another activation marker, CD69, was also expressed mainly by the $CD4^+$ population in the CD28-stimulated culture, while both $CD4^+$ and $CD8^+$ populations expressed CD69 after anti-CD3 stimulation (FIG. 7B).

Specific Example 5

CD28 ligation by PV-1 antibody selectively enhances the autologous MLR of $CD4^+$ T cells Next, the role of CD28 signaling in T cell reactivity to self APC was tested. In this experiment, spleen cells were applied to a nylon wool column and nylon wool non-adherent cells were collected and further purified into $CD4^+$ or $CD8^+$ cells by negative selection. Nylon wool adherent cells were obtained by temperature shift and agitation, and were inactivated by irradiation to be used as APC. $CD4^+$ or $CD8^+$ T cells were co-cultured with irradiated nylon-adherent cells in the presence or absence of titrated concentrations of PV-1 or 2C11. Seven days after cultivation, proliferation of responder T cells was measured by $^3H$-thymidine uptake. One representative result obtained from three experiments is shown in FIG. 8. In the presence of 2C11, strong proliferation was observed in both $CD4^+$ and $CD8^+$ T cells (FIG. 8A). In contrast, while $CD4^+$ T cells proliferated vigorously with PV-1 stimulation, very little proliferation was observed in the $CD8^+$ T cell population (FIG. 8B). The proliferative response of $CD4^+$ T cells to PV-1 was strongly inhibited by addition of F(ab) fragments of PV-1 (FIG. 8C), indicating that these responses are CD28-mediated. These results suggested that CD28-mediated signaling selectively triggers and/or enhances the autoreactivity of $CD4^+$ T cells to self APC in vivo.

Figure 9A:
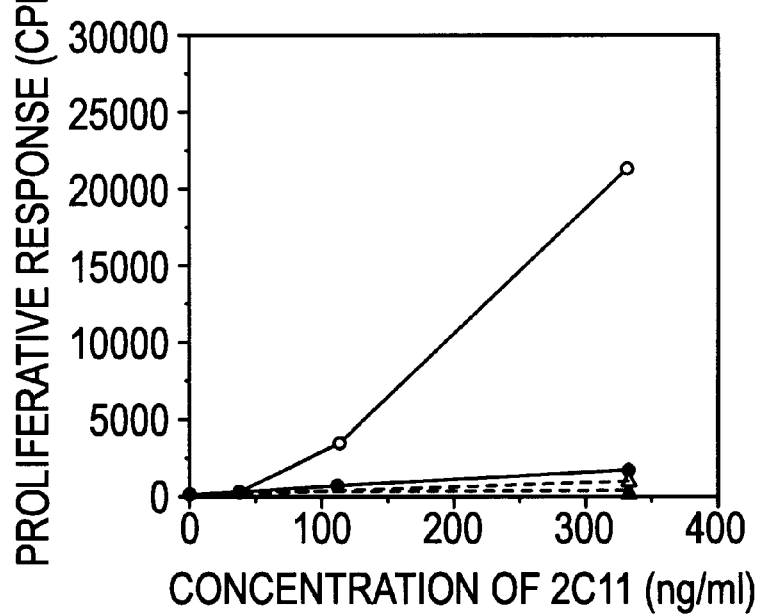
FIG. 9A is a plot of proliferation assessed by thymidine incorporation of CD4 and CD8 cells.
Figure 9B:
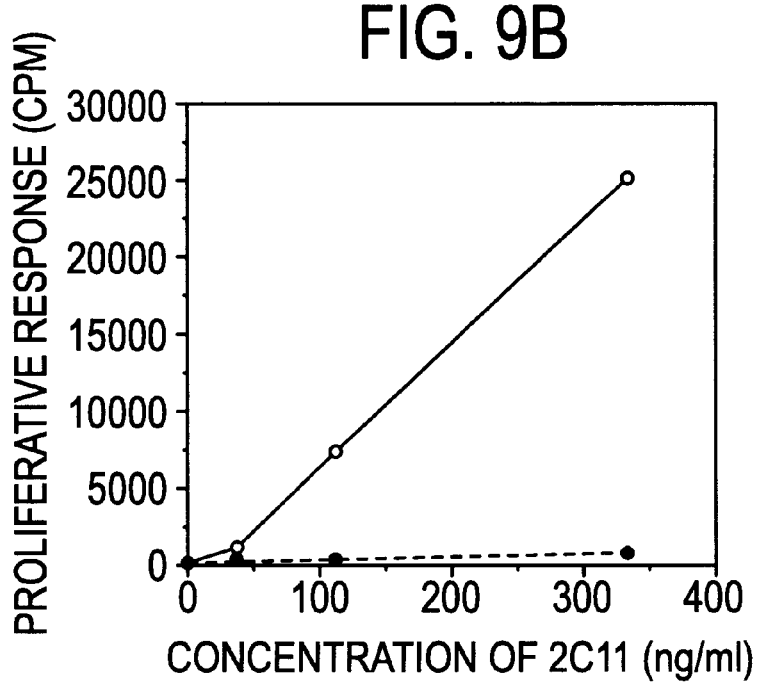
FIG. 9B is a plot of proliferation assessed by thymidine incorporation after $CTLA4_{Ig}$ or $control_{Ig}$ addition.

In order to determine whether the observed preferential activation of $CD4^+$ T cells induced by CD28 crosslinking occurs after native B7:CD28 T cell-APC interaction, we used B cells as a source of T cell costimulation, thereby ensuring physiologic presentation of costimulatory ligand(s) for CD28. Freshly isolated $CD4^+$ and $CD8^+$ T cells were cultured with syngeneic B cells in plastic plates which were coated with a low dose of anti-CD3 mAb 2C11. In the absence of B cells, both $CD4^+$ and $CD8^+$ cells showed marginal proliferation (FIG. 9). Under these conditions, freshly isolated B cells induced a strong proliferative response of $CD4^+$ T cells, whereas the proliferative response of the $CD8^+$ T cells was minimal (FIG. 9A). This $CD4^+$ T cell proliferative response to B cells was completely blocked by CTLA4-Ig fusion protein (FIG. 9B), indicating that the effect is B7 dependent. However, when a high dose of anti-CD3 was used for CD3 crosslinking (a dose that induced significant APC-independent proliferation), $CD8^+$ T cell proliferation was induced (data not shown). Therefore, the conditions that most likely mimick physiologic T:B APC interaction, i.e. low dose anti-CD3 and native B7 ligand, result in the preferential induction of $CD4^+$ cell proliferation, and furthermore, this correlates with preferential ability of anti-CD28 mAbs to induce calcium mobilization.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A hybridoma registered with The American Type Culture Collection (ATCC) as No. HB-12352 which is a supplemental deposit to No. HB 11944 producing a monoclonal antibody, PV-1, capable of binding to an epitope of mouse CD28.

2. The monoclonal antibody produced by the hybridoma of claim 1.

* * * * *